(12) United States Patent
La et al.

(10) Patent No.: US 12,318,424 B2
(45) Date of Patent: Jun. 3, 2025

(54) COMPOSITION FOR ENHANCING EXERCISE PERFORMANCE AND FATIGUE RECOVERY, CONTAINING FERMENTED RIPEN NONI, COCONUT SUGAR AND MUSCOVADO SUGAR AS ACTIVE INGREDIENTS

(71) Applicants: ATOMY OROT CO., LTD., Gongju-si (KR); NSTBIO CO., LTD., Gimpo-si (KR)

(72) Inventors: Im Joung La, Gongju-si (KR); Geum Su Seong, Gimpo-si (KR); Eun Young Park, Gimpo-si (KR); Yong Deok Kim, Gimpo-si (KR); Eun Min Kim, Gimpo-si (KR); Soo Jin Kim, Gimpo-si (KR)

(73) Assignees: ATOMY OROT CO., LTD., Gongju-si (KR); NSTBIO CO., LTD., Gimpo-si (KR)

( * ) Notice: Subject to any disclaimer, the term of this patent is extended or adjusted under 35 U.S.C. 154(b) by 0 days.

(21) Appl. No.: 18/175,099

(22) Filed: Feb. 27, 2023

(65) Prior Publication Data
US 2023/0218699 A1 Jul. 13, 2023

Related U.S. Application Data

(62) Division of application No. 17/646,464, filed on Dec. 29, 2021.

(30) Foreign Application Priority Data

Dec. 29, 2020 (KR) .......................... 10-2020-0185594
Nov. 24, 2021 (KR) .......................... 10-2021-0163434

(51) Int. Cl.
| | |
|---|---|
| *A61K 36/746* | (2006.01) |
| *A23G 3/48* | (2006.01) |
| *A23L 29/00* | (2016.01) |
| *A23L 33/105* | (2016.01) |
| *A61K 31/7004* | (2006.01) |
| *A61P 21/00* | (2006.01) |

(52) U.S. Cl.
CPC .............. *A61K 36/746* (2013.01); *A23G 3/48* (2013.01); *A23L 29/065* (2016.08); *A23L 33/105* (2016.08); *A61K 31/7004* (2013.01); *A61P 21/00* (2018.01)

(58) Field of Classification Search
None
See application file for complete search history.

(56) References Cited

FOREIGN PATENT DOCUMENTS

| CN | 101057700 A | 10/2007 |
|---|---|---|
| KR | 10-2005-0049617 A | 5/2005 |
| KR | 10-2009-0072555 A | 7/2009 |
| KR | 10-2047627 B1 | 12/2019 |
| KR | 10-2020-0040205 A | 4/2020 |
| KR | 10-2151372 B1 | 9/2020 |
| PH | 2/2013/000653 | 3/2014 |

OTHER PUBLICATIONS

English translation of Hwang (KR 20050049617) May 2005.*
English translation of Ma (CN 103005403 A), Apr. 3, 2013.*
International Search Report dated Apr. 7, 2022 in International Application No. PCT/KR2021/019831.
Medina, P.M.B., et al., "Effect of natrual and artificial sweeteners on the hemolymph glucose level (HGL) in *Drosophilia melanogaster*," International Journal of Biosciences, Jul. 14, 2015, 7(1):119-131.
Office Action dated Sep. 1, 2023 in U.S. Appl. No. 17/646,464.
Office Action dated Sep. 6, 2023 in U.S. Appl. No. 17/646,467.
Pulmuwon Green Juice Launches 'Noni & Calamansi', 2019, Retrieved from Internet: of http://www.newstown.co.kr/news/articleView.html? idxno=398766.
Office Action dated Mar. 10, 2023 in U.S. Appl. No. 17/646,464.
Screen captures from YouTube video clip entitled "Atomy Organic Fermented Noni Concentrate," 3 pages, uploaded on Nov. 28, 2020. Retrieved from Internet: <https://www.youtube.com/watch?v=O6Rq4x1NJ7M>.
Pulmuwon Green Juice Launches 'Noni & Calamansi'. Retrieved from Internet: of http://www.newstown.co.kr/news/articleView.html? idxno=398766, 2019.
Office Action dated Oct. 19, 2022 in Taiwanese Application No. 110149147.
Office Action dated Apr. 18, 2023 in U.S. Appl. No. 17/646,467.
Liu, C.-H., et al., "Extraction and Characterization of Antioxidant Compositions From Fermented Fruit Juice of *Morinda citrifolia* (Noni)," Agricultural Sciences in China, Dec. 2007, 6(12): 1494-1501.

(Continued)

*Primary Examiner* — Susan Hoffman
(74) *Attorney, Agent, or Firm* — Saliwanchik, Lloyd & Eisenschenk (57) ABSTRACT

The present invention relates to a composition for enhancing exercise capacity and recovery from fatigue containing fermented and aged noni, coconut sugar or muscovado sugar as an active ingredient, and more specifically, to a composition enhancing exercise capacity and recovery from fatigue, which has the effects of enhancing exercise capacity and inhibiting the accumulation of fatigue substances in blood by increasing glycogen storage in tissue and liver function. The present invention provides a food composition for exercise capacity enhancement and anti-fatigue, which is useful in the food industry. The composition of the present invention enables recovery from fatigue or enhancement of athletic ability to be achieved quickly by promoting the reduction of fatigue substances, and may provide sports drink products, functional food products and pharmaceutical composition products that are effective in enhancing recovery from fatigue and exercise capacity.

11 Claims, 3 Drawing Sheets

(56) References Cited

OTHER PUBLICATIONS

Office action dated Jan. 26, 2024 in U.S. Appl. No. 17/646,464.
Office Action dated Oct. 20, 2023 in U.S. Appl. No. 18/300,482.

* cited by examiner

COMPOSITION FOR ENHANCING EXERCISE PERFORMANCE AND FATIGUE RECOVERY, CONTAINING FERMENTED RIPEN NONI, COCONUT SUGAR AND MUSCOVADO SUGAR AS ACTIVE INGREDIENTS

CROSS-REFERENCE TO RELATED APPLICATIONS

This application is a divisional of Ser. No. 17/646,464, filed Dec. 29, 2021; which claims the benefit of Korean Application Nos. 10-2020-0185594, filed Dec. 29, 2020; and 10-2021-0163434, filed Nov. 24, 2021; the entire contents of which are incorporated herein by reference.

BACKGROUND

1. Technical Field

The present invention relates to a composition containing fermented and aged noni, coconut sugar or muscovado sugar as an active ingredient, and more particularly, to a composition for enhancing exercise capacity and recovery from fatigue, which has the effects of enhancing exercise capacity and inhibiting the accumulation of fatigue substances in blood by increasing glycogen storage in tissue and liver function, and thus is useful in the food industry.

2. Related Art

Generally, when muscles are not regularly trained, the muscular function will be impaired due to aging, and decreases in muscle mass and neuromuscular junctions (motor unit) will occur, and thus the body will feel fatigue easily and will become languid, thus reducing the vital power of the body and rapidly reducing the quality of life.

When a sign of fatigue appears, the body needs time to rest and recover, but in a busy modern society, it is difficult to properly keep the cycle of fatigue and recovery from fatigue. Accumulation of fatigue due to overwork may cause chronic fatigue, and may also cause many diseases such as peptic ulcer, hypertension, and diabetes. In addition, cancer, stroke, and heart disease are the three major causes of death in modern people, and are caused mainly by overwork.

The expression "accumulation of fatigue or stress" refers to a case in which mental and physical functions are not performed smoothly. Generally, fatigue may refer to a state in which the force required for muscle contraction activity is not sufficiently exerted, that is, a state in which exercise capacity is reduced. In contrast to physical fatigue, stress can be understood as a body rhythm imbalance resulting from mental overload. Thus, fatigue in a broad sense includes both fatigue and stress, and may refer to reduction in the ability to do physical or mental activities. Specifically, fatigue is mainly physical fatigue and refers to a state in which work efficiency is reduced, and stress is mental fatigue and refers to a state in which homeostasis is disrupted.

In order to inhibit accumulation of fatigue or stress, it is recommended to do regular exercise, such as resistance training, along with an appropriate diet. In recent years, with the "well-being" craze, the importance of exercise has been emphasized to enjoy a leisurely life and to inhibit and treat various adult diseases. As such, regular exercise is required to improve the quality of life, and not only athletes but also ordinary people tend to require more energy and endurance in daily life. Thus, studies on supplements, functional foods, food compositions and the like for improving physical exercise capacity have been conducted for a long period of time. In fact, it is known that the intake of compounds such as steroids and caffeine increases exercise capacity. However, such drugs can cause fatal side effects, and thus the use thereof is extremely limited.

It has been found that plants existing in nature contain large amounts of functional ingredients having bioregulatory functions, such as prevention of diseases and suppression of aging. Thus, studies on natural food materials have been actively conducted. In recent years, studies have been actively conducted to develop functional supplements using natural products with guaranteed safety, such as plant extracts.

Accordingly, the present inventors have conducted intensive studies on fermented and aged noni and coconut sugar, and as a result, have found that the intake of a complex of fermented and aged noni and coconut sugar increases exercise capacity and inhibits accumulation of blood fatigue factors, thereby completing the present invention.

PRIOR ART DOCUMENTS

Non-Patent Documents

1. Beck L., 2014, "Coconut sugar: Is it healthier than white sugar, or just hype?", The Globe & Mail, Retrieved 30 May 2015
2. Timothy P. E., 2016 Postprandial insulin and glucose levels are reduced in healthy subjects when a standardised breakfast meal is supplemented with a filtered sugarcane molasses concentrate. Eur. J. Nutr., 55 (8), 2365-2376

SUMMARY

An object of the present invention is to solve the above-described problems and other problems related thereto.

The present inventors have conducted studies on a composition comprising natural ingredients capable of effectively enhancing exercise capacity and recovery from fatigue, and as a result, have found that a composition containing fermented and aged noni, coconut sugar or muscovado sugar has an activity of enhancing exercise capacity and recovery from fatigue, thereby completing the present invention.

An object of the present invention is to provide a composition for enhancing exercise capacity and/or recovery from fatigue containing, as an active ingredient, fermented and aged noni, coconut sugar or muscovado sugar.

Another object of the present invention is to provide a method for producing a composition containing fermented and aged noni, coconut sugar or muscovado sugar.

Still another object of the present invention is to provide a food composition for enhancing exercise capacity and/or recovery from fatigue.

Yet another object of the present invention is to provide a pharmaceutical composition for enhancing exercise capacity and/or recovery from fatigue.

Still yet another object of the present invention is to provide a quasi-drug composition for enhancing exercise capacity and/or recovery from fatigue.

A further object of the present invention is to provide a feed composition for enhancing exercise capacity and/or recovery from fatigue.

The objects to be achieved according to the technical idea of the present invention disclosed in the present specification are not limited to the above-mentioned objects, and other objects not mentioned herein will be clearly understood by those skilled in the art from the following description.

The present invention will be described in detail below. Meanwhile, each description and embodiment disclosed in the present application may be applied to each other description and embodiment. That is, all combinations of various components disclosed in the present application fall within the scope of the present application. In addition, the scope of the present application is not construed as being limited by the detailed description described below.

To achieve the above-described objects, the present invention provides a composition for enhancing exercise capacity and/or recovery from fatigue containing, as an active ingredient, fermented and aged noni, coconut sugar and/or muscovado sugar.

Hereinafter, the present invention will be described in more detail.

As used herein, the term "fermented and aged noni" refers to noni obtained by fermenting and aging noni inoculated with lactic acid bacteria. Here, the part of noni that is used in the present invention is not limited, but noni fruits may be used as an example.

In the present invention, "fermented noni" may be a fermented product obtained by fermenting noni fruits inoculated with any one or more of the following 7 types of lactic acid bacteria:

(1) *Lactobacillus plantarum;*
(2) *Lactobacillus paracasei;*
(3) *Lactobacillus rhamnosus;*
(4) *Lactobacillus casei;*
(5) *Lactobacillus fermentum;*
(6) *Lactobacillus reuteri;* and
(7) *Lactococcus lactis* subsp. *lactis.*

In the present invention, the "fermented noni" may be one in which scopolin is bioconverted to scopoletin, and asperuloside is bioconverted to deacetylasperulosidic acid (DAA) and asperulosidic acid.

In the present invention, the content of bioconverted scopoletin in the "fermented noni" is 100 to 2,000 μg/g (based on the solid content (60%) of the fermented noni extract), the content of deacetylasperulosidic acid is 0.5 to 15 mg/g (based on the solid content (60%) of the fermented noni extract), and the content of asperulosidic acid is 0.2 to 5 mg/g (based on the solid content (60%) of the fermented noni extract).

In the present invention, the contents of scopoletin, deacetylasperulosidic acid and asperulosidic acid, which are functional ingredients contained in "fermented noni", are equal to those in "fermented and aged noni".

In the present invention, "fermented and aged noni" may be fermented and aged noni itself or an extract obtained therefrom. As an example, the fermented and aged noni of the present invention may be obtained by fermenting and aging noni fruits inoculated with lactic acid bacteria, and the liquid obtained by squeezing the fermented and aged noni may be an extract.

As used herein, the term "extract" commonly refers to a crude extract in the art, but in a broad sense also refers to a fraction obtained by fractionating the extract. That is, the fermented and aged noni extract includes not only one obtained using an extraction solvent, but also one obtained by subjecting the obtained one to a purification process. For example, the fermented and aged noni extract of the present invention also includes a fraction obtained by passing the extract through an ultrafiltration membrane with a predetermined molecular weight cut-off value, or a fraction obtained by additionally performing various purification methods such as various chromatography methods (designed for separation according to size, charge, hydrophobicity, or hydrophilicity).

In the present specification, the expression "containing as an active ingredient" means containing an amount sufficient to achieve the efficacy or activity of the fermented and aged noni or an extract thereof. In the present invention, since a composition containing an extract of the fermented and aged noni, which is a natural plant material, has no side effects on the human body even when the extract is administered in an excessive amount, the upper limit of the amount of the fermented and aged noni extract contained in the composition of the present invention may be selected within an appropriate range by those skilled in the art.

The fermented and aged noni extract according to the present invention is obtained by extraction using an organic solvent, and examples of an extraction solvent that may be used in the present invention are as follows.

First, suitable examples of polar solvents include (i) water, (ii) an alcohol having 1 to 6 carbon atoms (preferably, methanol, ethanol, propanol, butanol, n-propanol, iso-propanol, n-butanol, 1-pentanol, 2-butoxyethanol or ethylene glycol), (iii) acetic acid, (iv) DMFO (dimethyl formamide), and (v) DMSO (dimethyl sulfoxide).

Suitable examples of nonpolar solvents include acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride, methylene chloride, petroleum ether, and THF.

Preferred examples of an extraction solvent that may be used in the present invention include (a) water, (b) an anhydrous or lower alcohol having 1 to 4 carbon atoms (e.g., methanol, ethanol, propanol, butanol, etc.), (c) a mixture of the lower alcohol and water, (d) acetone, (e) ethyl acetate, (f) chloroform, (g) butyl acetate, (h) 1,3-butylene glycol, (i) hexane, and (j) diethyl ether. For easy extraction, extraction may be performed using water, ethanol, or a mixture of water and ethanol.

In addition, the fermented and aged noni extract that is used in the present invention may be produced in a powder form by additional processes such as distillation under reduced pressure and freeze-drying or spray-drying.

In the present invention, the fermented and aged noni and the coconut sugar may be contained at a weight ratio of 70:30 to 95:5, more preferably 80:20 to 90:10.

In addition, the fermented and aged noni and the muscovado sugar may be contained at a weight ratio of 70:30 to 95:5, more preferably 80:20 to 90:10.

In addition, the fermented and aged noni, the coconut sugar and the muscovado sugar may be contained at a weight ratio of 90:5:5 to 70:15:15, more preferably 90:5:5.

According to one aspect of the present invention, the present invention is directed to a food composition for enhancing exercise capacity or recovery from fatigue recovery containing fermented and aged noni, coconut sugar and/or muscovado sugar.

The food composition may include a health functional food composition. Examples of the health functional food composition include various foods, beverages, gum, tea, vitamin complexes, health supplements, etc. The health functional food composition may be used in the form of powders, granules, pills, tablets, capsules, candies, syrups or beverages. The food composition of each formulation may contain, in addition to the active ingredient, ingredients commonly used in the art, which may be appropriately selected by those skilled in the art without difficulty depending on the formulation or intended use of the composition. When the food composition is applied simultaneously with other raw materials, a synergistic effect may occur.

The composition may contain other ingredients, which may impart a synergistic effect to the main effect, within a range that does not impair the main effect of the present invention. For example, the composition may further contain additives such as fragrance, a colorant, a bactericide, an antioxidant, a preservative, a humectant, a thickener, an inorganic salt, an emulsifier, and a synthetic polymer, in order to improve physical properties thereof.

When the health functional food composition of the present invention is used as a food additive, the fermented and aged noni, coconut sugar, or muscovado sugar may be added as it is or used together with other foods or food ingredients, and may be appropriately used according to a conventional method. The content of the active ingredient may be suitably determined according to the intended use (prevention, health improvement or therapeutic treatment). The food is not particularly limited in the kind thereof. Examples of food to which the fermented and aged noni, coconut sugar, or muscovado sugar may be added include meat, sausage, bread, chocolate, candy, snacks, confectionery, pizza, ramen, other noodles, gums, dairy products including ice cream, various soups, beverages, teas, drinks, alcoholic beverages, vitamin complexes, etc., and include all health functional foods in the ordinary sense.

When the composition of the present invention is used as a health drink, it may contain various flavoring agents or natural carbohydrates as additional ingredients, like a conventional drink. Examples of the above-described natural carbohydrates include monosaccharides such as glucose and fructose, disaccharides such as maltose and sucrose, polysaccharides such as dextrin and cyclodextrin, and sugar alcohols such as xylitol, sorbitol and erythritol. As the flavoring agents, there may be used natural flavoring agents such as thaumatin or *stevia* extract, or synthetic flavoring agents such as saccharin or aspartame.

The present invention also provides a method for producing a composition containing fermented and aged noni, coconut sugar and/or muscovado sugar.

According to one aspect of the present invention, the present invention provides a method for producing a composition containing fermented and aged noni, coconut sugar and/or muscovado sugar, the method comprising steps of: obtaining fermented and aged noni by fermenting and/or aging noni using lactic acid bacteria; and adding coconut sugar and/or muscovado sugar to the fermented and aged noni, followed by aging.

Specifically, the present invention provides a method for producing a composition containing fermented and aged noni, coconut sugar and/or muscovado sugar, the method comprising steps of: (a) producing fermented and aged noni by fermenting and aging noni fruits inoculated with lactic acid bacteria; (b) squeezing the fermented and aged noni; and (c) adding and mixing coconut sugar and/or muscovado sugar with the fermented and aged noni.

In the present invention, the production method may further comprise step (d) of performing additional aging, after mixing the coconut sugar and/or the muscovado sugar with the fermented and noni in step (c).

In the present invention, the fermentation and aging may be performed at 35 to 40° C. for 48 to 168 hours, but the present invention is not limited thereto.

The aging may be performed by pouring the fermentation broth, produced in the fermentation process, over the fermentation product every 1 to 3 days, more specifically every 2 days.

In the present invention, sugar obtained by boiling the sap of a palm tree belonging to the belonging to the family Arecaceae, such as coconut (coco palm), palmyra palm, date palm, nipa palm, or sugar palm, is called palm sugar, and coconut sugar refers to palm sugar produced from the sap of the bud stem of a coconut palm and is a commercially available material.

The coconut sugar contains, as main components, 70 to 79% sucrose, 3 to 9% glucose and 3 to 9% fructose (Beck L., 2014, "Coconut sugar: Is it healthier than white sugar, or just hype?", The Globe & Mail, Retrieved 30 May 2015).

Muscovado sugar is unrefined sugar obtained by boiling sugar cane juice to form molasses. Muscovado sugar is dark brown granular sugar produced by pulverization after drying, and refers to sugar which is completely free from phosphoric acid, formic acid, sulfur dioxide, a preservative, or chemicals such as a bleaching agent or a viscosity modifier, which are used in refined sugar. Muscovado sugar has a higher molasses content than processed white sugar or brown sugar, and is strong in flavor and dark. It is a commercially available material.

According to one aspect of the present invention, the present invention is directed to a pharmaceutical composition for enhancing exercise capacity or recovery from fatigue containing fermented and aged noni, coconut sugar and/or muscovado sugar.

The pharmaceutical composition according to the present invention may contain the active ingredient alone or may be formulated in a suitable form together with a pharmaceutically acceptable carrier, and may further contain an excipient or a diluent. As used herein, the term "pharmaceutically acceptable" refers to a non-toxic composition which is physiologically acceptable and, when administered to the human beings, does not cause allergic reactions such as gastrointestinal disorders and dizziness, or similar reactions.

The pharmaceutical composition may further contain a pharmaceutically acceptable carrier such as a carrier for oral administration or a carrier for parenteral administration. Examples of the carrier for oral administration include lactose, starch, cellulose derivatives, magnesium stearate, stearic acid, and the like. In addition, various drug delivery materials that are used for oral administration of peptide formulations may be included. In addition, examples of the carrier for parenteral administration include water, suitable oil, saline, aqueous glucose and glycol, and the like, and further include a stabilizer and a preservative. Suitable stabilizers include antioxidants such as sodium hydrogen sulfite, sodium sulfite or ascorbic acid. Suitable preservatives include benzalkonium chloride, methyl- or propyl-paraben and chlorobutanol. The pharmaceutical composition of the present invention may further contain a lubricant, a wetting agent, a sweetening agent, a flavoring agent, an emulsifying agent, a suspending agent, and the like, in addition to the above-described ingredients. Other pharmaceutically acceptable carriers and agents may refer to those described in in Remington's Pharmaceutical Sciences, 19th ed., Mack Publishing Company, Easton, PA, 1995.

The composition of the present invention may be administered to mammals including humans by any method. For example, the composition may be administered orally or parenterally. Parenteral administration methods include, but are not limited to, intravenous, intramuscular, intraarterial, intramedullary, intrathecal, intracardiac, transdermal, subcutaneous, intraperitoneal, intranasal, enteral, topical, sublingual or rectal administration.

The pharmaceutical composition of the present invention may be formulated in an oral dosage form or a parenteral dosage form depending on the administration route as described above.

For oral dosage forms, the composition of the present invention may be formulated into a powder, granule, tablet, pill, dragee, capsule, liquid, gel, syrup, slurry, suspension, etc. using methods known in the art. For example, the oral dosage form may be obtained as a tablet or dragee by mixing the active ingredient with a solid excipient, pulverizing the mixture, adding a suitable adjuvant thereto, and processing the mixture into a granule mixture. Examples of suitable excipients include sugars such as lactose, dextrose, sucrose, sorbitol, mannitol, xylitol, erythritol and maltitol, starches such as corn starch, wheat starch, rice starch and potato starch, celluloses such as cellulose, methyl cellulose, sodium carboxymethyl cellulose and hydroxypropylmethyl cellulose, and fillers such as gelatin and polyvinylpyrrolidone. In addition, if necessary, cross-linked polyvinylpyrrolidone, agar, alginic acid or sodium alginate may be added as a disintegrant. Furthermore, the pharmaceutical composition of the present invention may further contain an anti-aggregating agent, a lubricant, a wetting agent, a flavoring agent, an emulsifying agent, and a preservative.

For parenteral dosage forms, the pharmaceutical composition may be formulated in the form of an injection, cream, lotion, external ointment, oil, humectant, gel, aerosol or nasal inhalant by methods known in the art. These formulations are described in Remington's Pharmaceutical Science, 19th ed., Mack Publishing Company, Easton, PA, 1995, which is a prescription commonly known in all pharmaceutical chemistries.

The total effective amount of the composition of the present invention may be administered to a patient in a single dose, and may be administered in multiple doses by a fractionated treatment protocol over a prolonged period of time. The pharmaceutical composition of the present invention may have varying contents of the active ingredient depending on the severity of the disease. Preferably, the preferred total dose of the pharmaceutical composition of the present invention may be about 0.01 μg to 10,000 mg, preferably 0.1 μg to 500 mg, most preferably 100 mg to 500 mg per kg of patient body weight per day. However, the effective dose of the pharmaceutical composition to be administered to a patient is determined in consideration of various factors, including the formulation method, the route of administration and the number of treatments, as well as the patient's age, weight, health status and sex, the severity of the disease, diet, and excretion rate, and thus those of ordinary skill in the art will be able to determine an appropriate effective dosage of the composition of the present invention in consideration of these factors. The pharmaceutical composition according to the present invention is not particularly limited in its formulation, administration route and administration method, as long as it exhibits the effect of the present invention.

According to one aspect of the present invention, the present invention is directed to a quasi-drug composition for enhancing exercise capacity or recovery from fatigue containing fermented and aged noni, coconut sugar and/or muscovado sugar.

As used herein, the term "quasi-drug" refers to a product which, among the products being used for the purpose of treatment, alleviation, handling, or prevention of human or animal diseases, excludes those which are not a tool, a machine, or a device, and a product which, among the products being used for the purpose of rendering a pharmacological effect on the human or animal structures and functions, excludes those which are not a tool, a machine, or a device.

In one embodiment, the quasi-drug may include an agent for internal administration, but is not limited thereto, and the formulation method, dose, use method, components, etc. of the quasi-drug may be appropriately selected using conventional techniques known in the art.

The quasi-drug composition of the present invention may further contain, in addition to the above ingredient, a pharmaceutically acceptable carrier, excipient or diluent, if necessary. The pharmaceutically acceptable carrier, excipient or diluent is not limited as long as it does not impair the effects of the present invention, and examples thereof include a filler, an extender, a binder, a wetting agent, a disintegrant, a surfactant, a lubricant, a sweetener, a fragrance, and a preservative.

According to one aspect of the present invention, the present invention is directed to a feed composition for enhancing exercise capacity or recovery from fatigue containing fermented and aged noni, coconut sugar and/or muscovado sugar.

In the present invention, the feed composition may be formulated in a conventional feed form, and may also contain known feed ingredients. In addition, the feed composition may be used as a feed additive, which is added in the form of an additive to the feed used. The feed additive of the present invention corresponds to a supplementary feed under the Feed Management Act, and may further contain minerals such as sodium bicarbonate (soda), bentonite, magnesium oxide, and composite minerals, trace minerals such as zinc, copper, cobalt, and selenium, vitamins such as carotene, vitamin E, vitamins A, D, E, nicotinic acid, and vitamin B complexes, protective amino acids such as methionine and lysine, protective fatty acids such as fatty acid calcium salts, live bacteria such as probiotics (lactic acid bacteria), yeast cultures, and fungal fermentation products, yeast agents, etc.

The feed or feed additive of the present invention may be applied to diets for a number of animals, including mammals, poultry and fish.

The complex of the fermented and aged noni and coconut sugar or muscovado sugar contained in the composition for enhancing exercise capacity and recovery from fatigue according to the present invention has the effect of enhancing exercise capacity and recovery from fatigue.

In addition, the fermented and aged noni has contains bioconverted components (scopoletin, deacetylasperulosidic acid and asperulosidic acid), which are obtained in the process of fermenting noni fruits and are capable of improving digestion and absorption, and thus it promotes digestion, absorption, and bowel movement in adults and the elderly who have relatively low digestibility. In addition, the fermented and aged noni is a natural raw material, and thus has no toxicity or side effects and may be safe to consume.

In addition, the process of producing the fermented and aged noni may greatly reduce the production cost, thereby greatly reducing the cost burden of consumers.

In addition, the composition containing the complex of the fermented and aged noni and the coconut sugar or the muscovado sugar has improved sensory characteristics compared to conventional noni, and thus is a food composition that consumers can enjoy without burden.

DETAILED DESCRIPTION

Hereinafter, the present invention will be described in more detail with reference to the following examples. However, these examples serve merely to illustrate the present invention, and the scope of the present invention is not limited to these examples.

Compositions for enhancing exercise capacity and recovery from fatigue were produced through the following process.

Example 1: Production of Compositions for Enhancing Exercise Capacity and Recovery from Fatigue 1.1: Production of Fermented and Aged Noni 690 kg of noni fruits were inoculated with complex lactic acid bacteria (a complex of 7 types of lactic acid bacteria, AON1805, Lactomason Co., Ltd.) and fermented at 37° C. for 45 days or more. Fermentation and aging were performed while 10 L of the fermentation broth collected every 7 days from the start date of fermentation was poured over the noni fruits. The composition of the complex lactic acid bacteria (a complex of 7 types of lactic acid bacteria, AON1805, Lactomason Co., Ltd.) is shown in Table 1 below. After completion of the aging, the fermented and aged noni was squeezed and the solid was removed, thus obtaining a fermented and aged noni extract.

TABLE 1

Raw material name or ingredient name and mixing ratio

| No. | Raw material name or ingredient name | Mixing ratio (%) |
|---|---|---|
| 1 | Lactobacillus plantarum | 70% |
| 2 | Lactobacillus rhamnosus | 5% |
| 3 | Lactobacillus casei | 5% |
| 4 | Lactobacillus fermentum | 5% |
| 5 | Lactobacillus paracasei | 5% |
| 6 | Lactobacillus reuteri | 5% |
| 7 | Lactococcus lactis subsp. lactis | 5% |

1.2: Production of Coconut Sugar

Juice was collected from the flower stalks of a coconut tree, and then the coconut flower stalk juice was concentrated into marmalade by stirring while heating at 90° C. according to a traditional method, and then hardened. The completely hardened material was finely pulverized to obtain coconut sugar.

1.3: Production of Muscovado Sugar

The leaves and impurities of harvested sugar cane were removed, and the juice squeezed from the sugar cane was boiled in a large pot for a sufficient time. Then, the floating impurity and the precipitate were removed, and when the residue reached a water-evaporated state, it was dried with stirring until it reached a powdery state. Then, the dried material was finely pulverized to obtain muscovado sugar.

1.4: Production of Complexes Using Fermented and Aged Noni and Coconut Sugar

The fermented and aged noni extract produced in Example 1.1 and the coconut sugar produced in Example 1.2 were mixed together at various ratios and then aged for 15 days to obtain complexes.

[Complex Production]
  Complex 1: 90 wt % fermented and aged noni extract: 10 wt % coconut sugar
  Complex 2: 80 wt % fermented and aged noni extract: 20 wt % coconut sugar
  Complex 3: 70 wt % fermented and aged noni extract: 30 wt % coconut sugar 1.5: Production of Complexes Using Fermented and Aged Noni and Muscovado Sugar The fermented and aged noni extract produced in Example 1.1 and the muscovado sugar produced in Example 1.3 were mixed together at various ratios and then aged for 15 days to obtain complexes.

[Complex Production]
  Complex 4: 90 wt % fermented and aged noni extract: 10 wt % muscovado sugar
  Complex 5: 80 wt % fermented and aged noni extract: 20 wt % muscovado sugar
  Complex 6: 70 wt % fermented and aged noni extract: 30 wt % muscovado sugar 1.6: Production of Complexes Using Fermented and Aged Noni, Coconut Sugar and Muscovado Sugar The fermented and aged noni, coconut sugar and muscovado sugar produced in Examples 1.1 to 1.3, respectively, were mixed together at various ratios and then aged for 15 days to obtain complexes.

[Complex Production]
  Complex 7: 90 wt % fermented and aged noni: 5 wt % coconut sugar: 5 wt % muscovado sugar
  Complex 8: 80 wt % fermented and aged noni: 10 wt % coconut sugar: 10 wt % muscovado sugar
  Complex 9: 70 wt % fermented and aged noni: 15 wt % coconut sugar: 15 wt % muscovado sugar 1.7: Production of Complex Using Fermented and Aged Noni and Unrefined Sugar The fermented and aged noni extract produced in Example 1.1 and unrefined sugar were mixed together at various ratios and then aged for 15 days to obtain a complex.
[Complex Production]
Complex 10: 90 wt % fermented and aged noni: 10 wt % unrefined sugar Experimental Example 1: Test for Enhancement of Exercise Capacity The exercise capacity enhancement effects of the extract or sugar produced in each of Examples 1.1 to 1.3 and the complex produced in each of Examples 1.4 to 1.6 were evaluated.
(1) Fatigue Induction in Mice
ICR mice (Orient Bio, Korea), each weighing 30 g, were purchased and adapted for 1 week at a temperature of 20° C. to 24° C. and a humidity of 55% with a 12-hr light/12-hr dark cycle. Then, the experimental animals were divided into experimental groups (8 mice per group) as follows: experimental group 1 (non-exercise group; hereinafter referred to as normal); experimental group 2 (exercise control group; hereinafter referred to as control); experimental group 3 (a group to which 100 mg/kg of fermented and aged noni was administered; hereinafter referred to as FN); experimental group 4 (a group to which 100 mg/kg of coconut sugar was administered; hereinafter referred to as CS); experimental group 5 (a group to which 100 mg/kg of muscovado sugar was administered; hereinafter referred to as MS); experimental group 6 (a group to which 100 mg/kg of complex 10 was administered; hereinafter referred to as FNS); experimental group 7 (a group to which 100 mg/kg of complex 1 was administered; hereinafter referred to as C 1); experimental group 8 (a group to which 100 mg/kg of complex 2 was administered; hereinafter referred to as C 2); experimental group 9 (a group to which 100 mg/kg of complex 3 was administered; hereinafter referred to as C 3); experimental group 10 (a group to which 100 mg/kg of complex 4 was administered; hereinafter referred to as C 4); experimental group 11 (a group to which 100 mg/kg of complex 5 was administered; hereinafter referred to as C 5); experimental group 12 (a group to which 100 mg/kg of complex 6 was administered; hereinafter referred to as C 6); experimental group 13 (a group to which 100 mg/kg of complex 7 was administered; hereinafter referred to as C 7); experimental group 14 (a group to which 100 mg/kg of complex 8 was administered; hereinafter referred to as C 8); and experimental group 15 (a group to which 100 mg/kg of complex 9 was administered; hereinafter referred to as C 9). Each test substance was administered once a day for a total of 4 weeks.
(2) Measurement of Exercise Capacity after Each Complex
Each experiment animal was maintained in a stable state from 16 hours before the start of the experiment under the breeding conditions, and then forced to swim in an acrylic plastic water bath (70 cm×70 cm×60 cm), about 70% of which was filled with water. Regarding the swimming time, the state in which the experimental animal was exhausted and no longer moving was set as the end point, and the time from the start time to the end time was measured as the swimming time.

Figure 1:
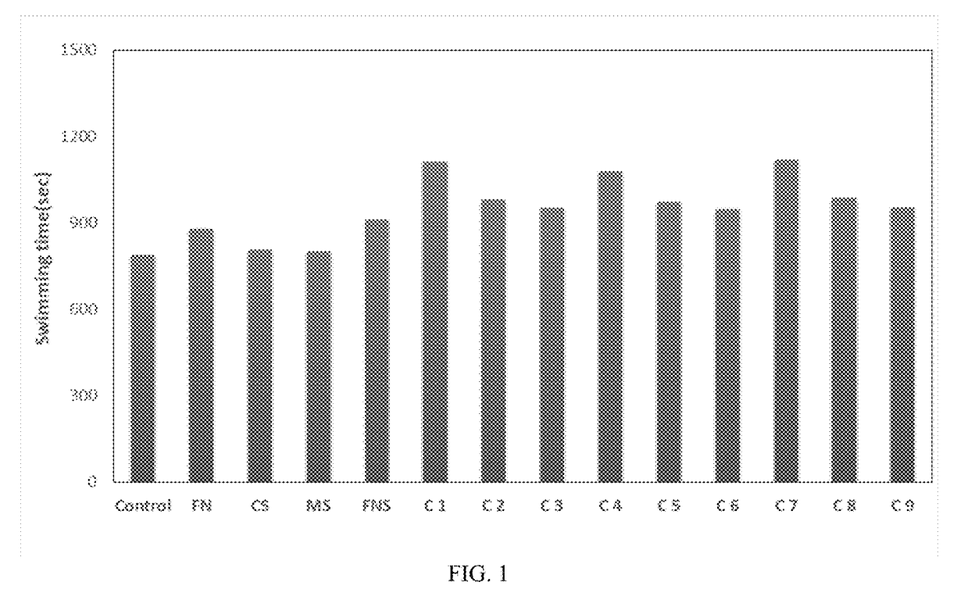
FIG. 1 is a graph showing the results of measuring the swimming time in a forced swimming test for a control group, groups to which fermented and aged noni, coconut sugar or muscovado sugar was administered alone, and groups to which a complex of fermented and aged noni and at least one of coconut sugar or muscovado sugar was administered, in one example of the present invention.

As a result, as shown in FIG. 1, the swimming time to exhaustion was measured to evaluate exercise capacity. As a result of the experiment, it was confirmed that, under the same concentration condition, the swimming time more increased in all the groups treated with each complex of the present invention than in the extract or sugar group (to which fermented and aged noni, coconut sugar or muscovado sugar was administered alone) compared to the control group, suggesting that administration of each complex more enhances exercise capacity than administration of the extract or sugar alone. In particular, it could be confirmed that the groups, to which each of complexes 1, 4 and 7 was administered, showed the longest swimming time (1081 to 1119 seconds), and thus had excellent exercise capacity.

Meanwhile, it was shown that the swimming time in the FNS group to which a complex of the fermented and aged noni extract and unrefined sugar was administered was 813 seconds, which is significantly shorter than those in the groups to which each of complexes 1, 4 and 7 was administered.

These results show that the exercise capacity enhancement effect of the complex of the fermented and aged noni and at least one of coconut sugar and muscovado sugar is better than the exercise capacity enhancement effect of coconut sugar and muscovado sugar alone.

As a result of the behavioral experiment, it can be seen that the composition of the present invention may increase the movement distance and exercise time, and may enhance exercise capacity. In addition, the composition may increase the blood glucose concentration, and may also increase the concentration of glycogen in muscle and decrease the concentration of lactate dehydrogenase (LDH) in muscle.

Experimental Example 2: Test for Enhancement of Recovery from Fatigue (1) Measurement of Lactate Concentration
After an experiment was conducted according to Experimental Example 1, the mice were subjected to a forced swimming test on the day of the end of administration, and the production of blood lactate, which is a typical fatigue substance, was measured.

Each experiment animal was maintained in a stable state from 16 hours before the start of the experiment under the breeding conditions, and then forced to swim in an acrylic plastic water bath (70 cm×70 cm×60 cm), about 70% of which was filled with water. All the experimental animals were forced to swim for 15 minutes. After swimming, in order to measure muscle fatigue after aerobic exercise, blood was collected from the tail at 10-minute intervals at rest, and the serum lactate concentration was measured using a lactate meter (Lactate Pro LT-1710, ARKRAY Inc., Japan).

Figure 2:
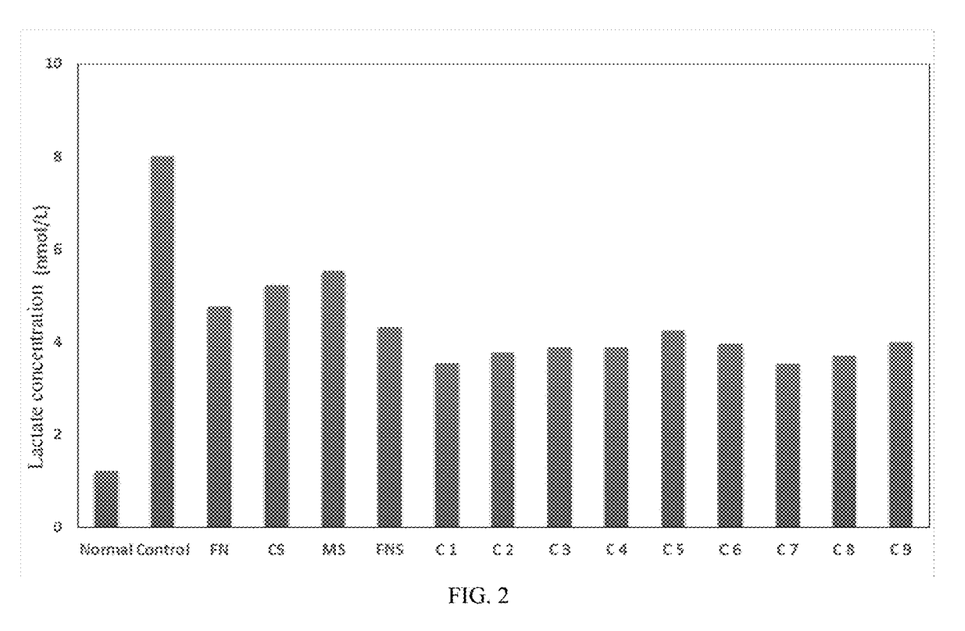
FIG. 2 is a graph showing the results of measuring the blood lactate concentration after forced swimming for a control group, groups to which fermented and aged noni, coconut sugar or muscovado sugar was administered alone, and groups to which a complex of fermented and aged noni and at least one of coconut sugar or muscovado sugar was administered, in one example of the present invention.

As a result, as shown in FIG. 2, it was confirmed that the lactate concentration immediately after swimming increased by 6.5 times or more compared to that in the stable period, and under the same concentration condition, the blood lactate concentration significantly decreased in the complex-administered groups compared to the control group and the groups to which the fermented and aged noni, coconut sugar and muscovado sugar were administered alone.

In particular, it could be confirmed that, under the same concentration condition, the experimental group, to which each complex of the present invention was administered, showed a lactate concentration which is 4 to 55% lower than the control group, suggesting that each complex of the present invention significantly reduces lactate which is a substance that causes muscle fatigue.

In particular, it was confirmed that the lactate concentration in the FNS group, to which a complex of the fermented and aged noni extract and unrefined sugar was administered, was about 4.34, which is significantly higher than those in the groups to which each of complexes 1 (C 1), 4 (C 4) and 7 (C 7) was administered.

Thereby, it was confirmed that the complex of the present invention promotes recovery from fatigue, and thus has an excellent effect of enhancing exercise capacity.

(2) Blood Chemical Test after Swimming Fatigue

After an experiment was conducted according to Experimental Example 1, the mice were subjected to a forced swimming test on the day of the end of administration, and then euthanized. Blood was collected from the heart, and the inorganic phosphorus concentration and creatine kinase (CK) concentration in the separated serum were measured with an automatic analyzer by the Green Cross Research Institute.

During exercise, ATP in muscle is hydrolyzed in the stage of increasing the affinity of myosin and actin by repeated muscle contractions, thereby rapidly increasing the serum inorganic phosphorus concentration. It is known that when the serum inorganic phosphorus concentration rapidly increases during exercise, the cross-bridge of the muscle fiber is weakened and force generation is reduced. Accordingly, the serum inorganic phosphorus concentration is used as an important indicator of muscle fatigue.

Figure 3:
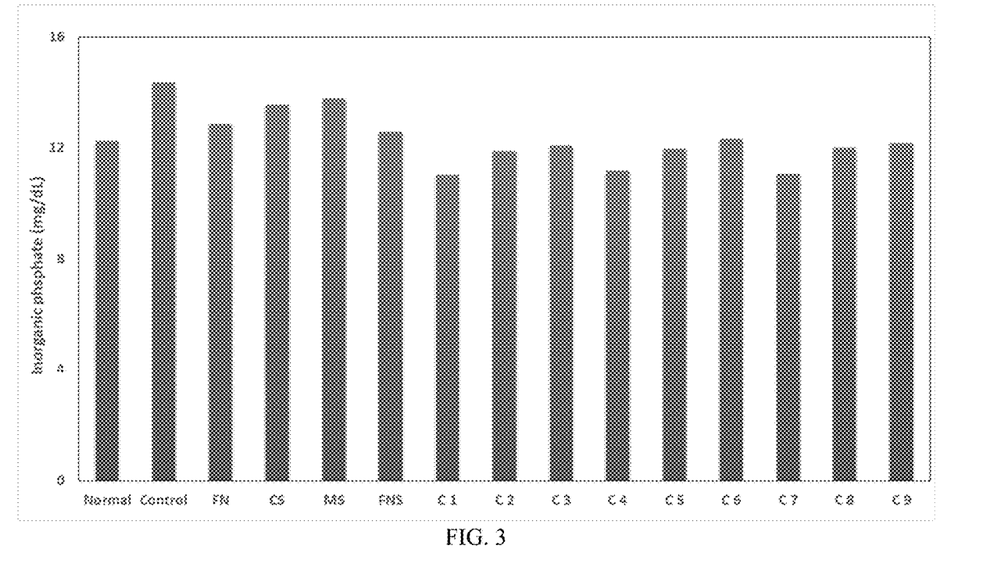
FIG. 3 is a graph showing the results of the serum inorganic phosphorus concentration after forced swimming for a control group, groups to which fermented and aged noni, coconut sugar or muscovado sugar was administered alone, and groups to which a complex of fermented and aged noni and at least one of coconut sugar or muscovado sugar was administered, in one example of the present invention.

As a result, as shown in FIG. 3, it was confirmed that the serum inorganic phosphorus concentration significantly decreased in all the complex-administered groups compared to the exercise control group. The groups, to which each of complexes 1, 4 and 7 was administered, showed the lowest values of 11.01 mg/dL, 11.18 mg/dL and 11.07 mg/dL, respectively, suggesting that these complexes are effective in recovering from fatigue by reducing the serum inorganic phosphorus concentration which is a fatigue factor.

Meanwhile, the FNS group, to which a complex of the fermented and aged noni extract and unrefined sugar was administered, showed a serum inorganic phosphorus concentration of 12.58 mg/dL, which is significantly lower than that in the exercise control group but is similar to that in the group to which the fermented and aged noni was administered alone.

Meanwhile, it was confirmed that the serum inorganic phosphorus level in the FNS group was higher than those in the groups to which each of complexes 1, 4 and 7 was administered.

Creatine kinase (EC 2.7. 3.2) is an enzyme discovered in skeletal muscle by K. Lohmans in 1943. It is an enzyme that catalyzes the reaction of creatine and ATP to produce creatine phosphate. It catalyzes the Roman reaction of phosphocreatine+ADP creatine+ATP (a reaction that transfers a high-energy phosphate group from phosphocreatine to ADP to synthesize ATP). Creatine kinase is abundant in muscle, and when a large amount of ATP is consumed upon contraction of skeletal muscle, creatine kinase produces and supplies ATP from a large amount of phosphocreatine present in the muscle.

Figure 4:
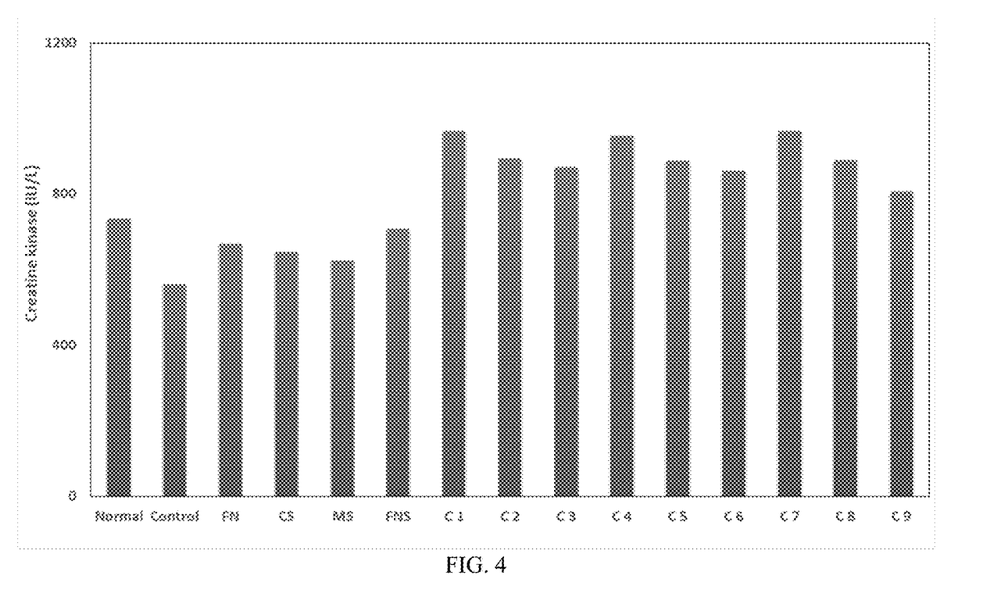
FIG. 4 is a graph showing the results of the serum creatine kinase concentration after forced swimming for a control group, groups to which fermented and aged noni, coconut sugar or muscovado sugar was administered alone, and groups to which a complex of fermented and aged noni and at least one of coconut sugar or muscovado sugar was administered, in one example of the present invention.
Figure 5:
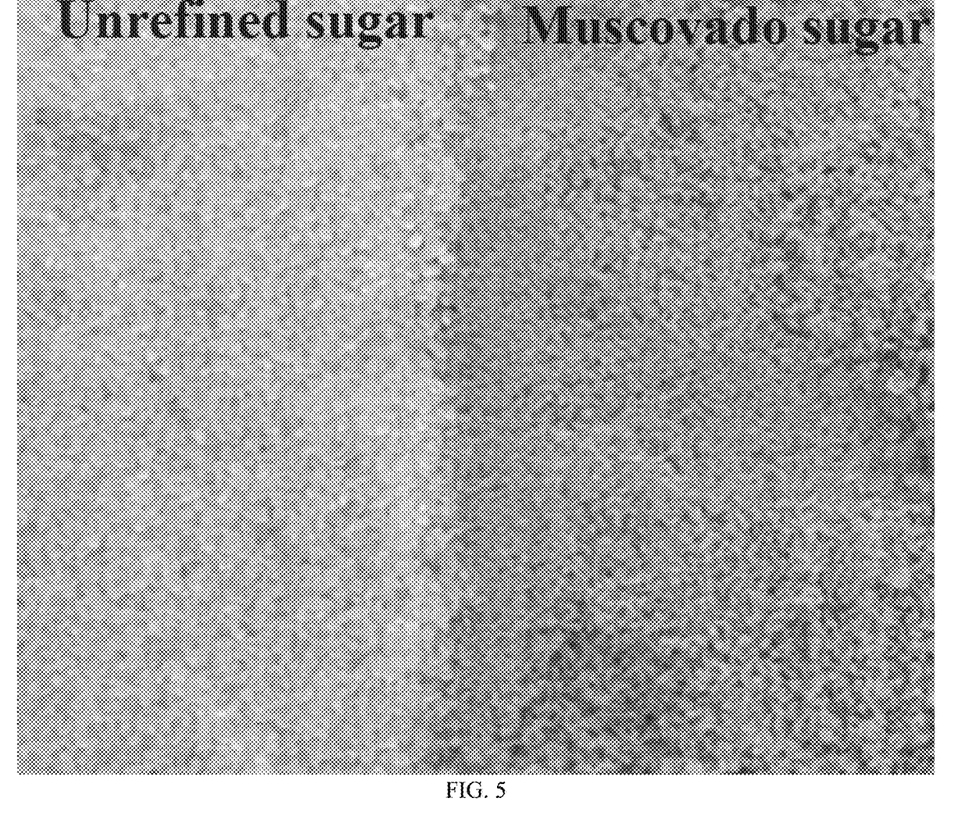
FIG. 5 shows the difference in crystal and sensory characteristics (morphology) between unrefined sugar and muscovado sugar.

As a result of the experiment, as shown in FIG. 4, it was confirmed that the creatine kinase concentration in the exercise control group was 562 IU/L, and the creatine kinase concentrations in the groups, to which fermented and aged noni or sugar was administered alone, and in the complex-administered groups, were all higher than that in the exercise control group.

In particular, it could be confirmed that the groups, to which each of complex 1 (C 1), complex 4 (C 4) and complex 7 (C 7) was administered, showed the highest creatine kinase concentrations of 967 IU/L, 955 IU/L and 966 IU/L, respectively, suggesting that these complexes are effective in alleviating muscle fatigue by promoting ATP resynthesis under the same concentration condition.

In addition, it was confirmed that the creatine kinase concentration in the FNS group, to which a complex of the fermented and aged noni and unrefined sugar was administered, was significantly low (709 IU·L) compared to those in the groups to which each of complexes 1, 4 and 7 was administered.

While the present invention has been described with reference to the particular illustrative embodiments, those of ordinary skill in the art to which the present invention pertains will appreciate that the present invention may be embodied in other specific forms without departing from the technical spirit or essential characteristics of the present disclosure. Therefore, the embodiments described above are considered to be illustrative in all respects and not restrictive. The scope of the present invention should be defined by the claims rather than the foregoing description, and it should be understood that all modifications or variations derived from the meanings and scope of the present invention and equivalents thereof are included in the scope of the appended claims.

What is claimed is:

1. A method for producing a composition comprising an extract of fermented and aged noni, coconut sugar and muscovado sugar, the method comprising steps of:
   (a) obtaining fermented and aged noni by an initial fermenting and aging of noni using lactic acid bacteria;
   (b) obtaining fermented and aged noni extract by extraction of the fermented and aged noni using a polar or nonpolar solvent; and
   (c) adding coconut sugar and muscovado sugar to the fermented and aged noni extract, followed by additional aging;
   wherein the initial fermentation and aging is performed at 35 to 40° C. for at least 48 hours,
   wherein the fermented and aged noni extract, the coconut sugar, and the muscovado sugar are contained at a weight ratio of 90:5:5,
   wherein the fermented and aged noni is obtained by fermenting and aging noni fruits inoculated with a complex of lactic acid bacteria, wherein aging comprises pouring a fermentation broth collected from the fermentation over the noni fruits, and
   wherein the complex of lactic acid bacteria comprises *Lactobacillus plantarum, Lactobacillus rhamnosus, Lactobacillus casei, Lactobacillus fermentum, Lactobacillus paracasei, Lactobacillus reuteri,* and *Lactococcus lactis* subsp. *lactis.*

2. The method of claim 1, wherein the additional aging of the complex of fermented and aged noni extract with added coconut sugar and muscovado sugar is for a period of 15 days.

3. The method of claim 1, wherein the solvent is a polar solvent.

4. The method of claim 3, wherein the polar solvent is water.

5. The method of claim 3, wherein the polar solvent is an alcohol having 1 to 6 carbon atoms.

6. The method of claim 5, wherein the polar solvent is an alcohol selected from the group consisting of methanol, ethanol, propanol, butanol, n-propanol, iso-propanol, n-butanol, 1-pentanol, 2-butoxyethanol, and ethylene glycol.

7. The method of claim 3, wherein the polar solvent is acetic acid.

8. The method of claim 3, wherein the polar solvent is dimethyl sulfoxide.

9. The method of claim 1, wherein the solvent is a nonpolar solvent.

10. The method of claim 9, wherein the nonpolar solvent is selected from the group consisting of acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride, methylene chloride, petroleum ether, and THF.

11. The method of claim 1, wherein the complex of lactic acid bacteria consists of *Lactobacillus plantarum, Lactobacillus rhamnosus, Lactobacillus casei, Lactobacillus fermentum, Lactobacillus paracasei, Lactobacillus reuteri*, and *Lactococcus lactis* subsp. *lactis*.

\* \* \* \* \*